(12) United States Patent
Klumb et al.

(10) Patent No.: US 6,572,648 B1
(45) Date of Patent: Jun. 3, 2003

(54) ENDOLUMINAL PROSTHESIS AND TISSUE SEPARATION CONDITION TREATMENT METHOD

(75) Inventors: Katherine J. Klumb, Los Altos, CA (US); Thomas J. Fogarty, Portola Valley, CA (US); Kirti P. Kamdar, Sunnyvale, CA (US); Bradley B. Hill, Portola Valley, CA (US)

(73) Assignee: Vascular Architects, Inc., San Jose, CA (US)

( * ) Notice: Subject to any disclaimer, the term of this patent is extended or adjusted under 35 U.S.C. 154(b) by 117 days.

(21) Appl. No.: 09/608,281

(22) Filed: Jun. 30, 2000

(51) Int. Cl.[7] ................................................. A61F 2/06
(52) U.S. Cl. ...................................... 623/1.15; 623/1.22
(58) Field of Search ............................... 623/1.13, 1.15, 623/1.22; 606/108, 191

(56) References Cited

U.S. PATENT DOCUMENTS

| | | | |
|---|---|---|---|
| 4,553,545 A | 11/1985 | Maass et al. | |
| 4,760,849 A | 8/1988 | Kropf | |
| 4,795,458 A | 1/1989 | Regan | |
| 4,886,062 A | 12/1989 | Wiktor | |
| 4,913,141 A | 4/1990 | Hillstead | |
| 5,037,427 A | 8/1991 | Harada et al. | |
| 5,133,732 A * | 7/1992 | Wiktor | 606/195 |
| 5,147,370 A | 9/1992 | McNamara et al. | |
| 5,282,823 A * | 2/1994 | Schwartz et al. | 606/198 |
| 5,607,445 A * | 3/1997 | Summers | 606/198 |
| 5,772,668 A | 6/1998 | Summers et al. | |
| 5,824,052 A * | 10/1998 | Khosravi et al. | 623/1 |
| 5,824,053 A | 10/1998 | Khosravi et al. | |
| 5,833,699 A * | 11/1998 | Chuter | 606/198 |
| 6,019,779 A | 2/2000 | Thorud et al. | |
| 6,027,516 A | 2/2000 | Kolobow et al. | |
| 6,090,134 A | 7/2000 | Tu et al. | |
| 6,364,904 B1 * | 4/2002 | Smith | 623/1.22 |
| 2002/0004679 A1 * | 1/2002 | Eury et al. | |

FOREIGN PATENT DOCUMENTS

| | | | |
|---|---|---|---|
| DE | 297 21 310 | 2/1998 | |
| FR | 2 671 482 A1 * | 7/1992 | ............ A61F/2/06 |
| GB | 2 270 264 A | 3/1994 | |

OTHER PUBLICATIONS

D. Maass, Ch. L. Zollikofer, F. Largiadèr, and A. Senning, "Radiological Follow-up of Transluminally Inserted Vascular Endoprostheses: An Experimental Study Using Expanding Spirals," Radiology, 1984, vol. 152, No. 3, pp. 659–663.
Instruction Manual for Wallstent® Transhepatic Biliary Endoprosthesis with the Unistep™ Delivery System, Schneider (USA), Inc.–Pfizer Hospital Products Group, 4 pages.

* cited by examiner

*Primary Examiner*—David H. Willse
*Assistant Examiner*—Javier G. Blanco
(74) *Attorney, Agent, or Firm*—James F. Hann; Haynes Beffel & Wolfeld LLP

(57) ABSTRACT

An endoluminal prosthesis includes a coiled body and a graft material covering at least part of the coiled body to create a coiled stent graft. The average stent graft diameter to turns width ratio may be about 0.8 to 1 to about 2.4 to 1 when expanded.

17 Claims, 12 Drawing Sheets

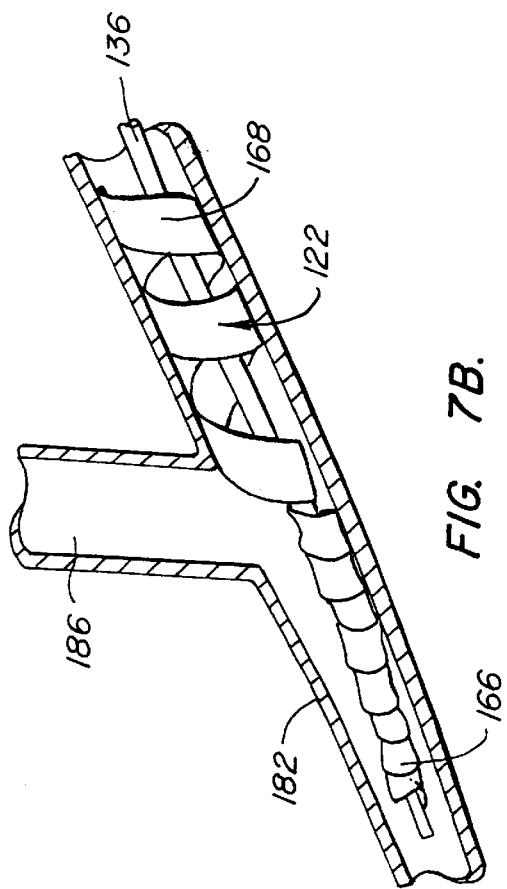
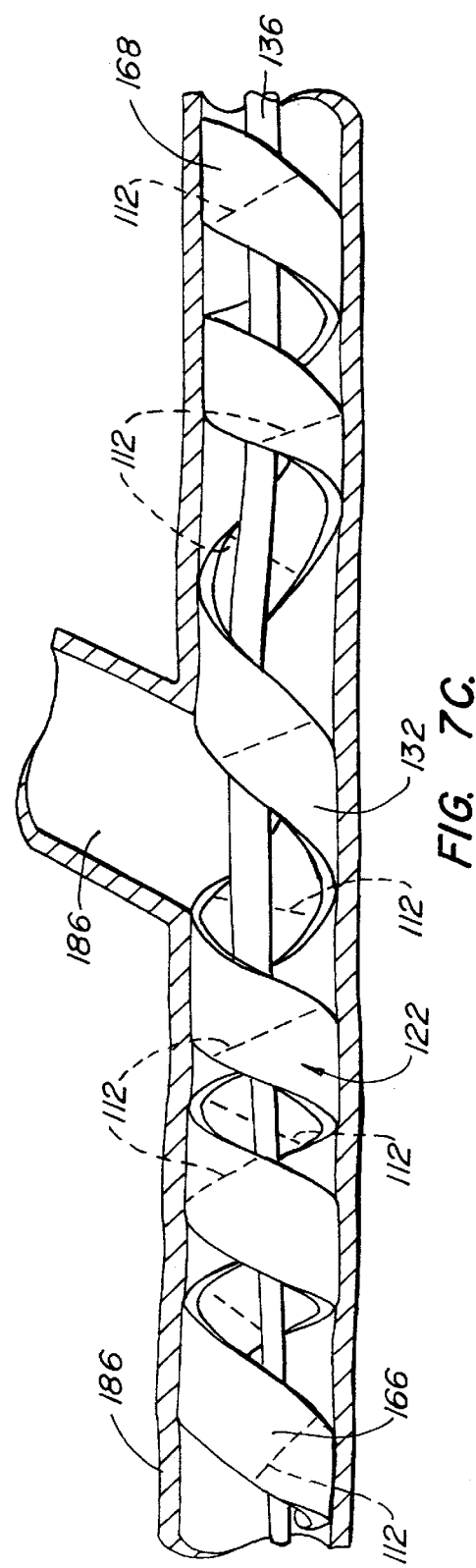

ENDOLUMINAL PROSTHESIS AND TISSUE SEPARATION CONDITION TREATMENT METHOD

CROSS-REFERENCE TO RELATED APPLICATIONS

This is related to the following: U.S. patent application Ser. No. 09/258,542 filed Feb. 26, 1999, U.S. patent application Ser. No. 09/400,952 filed Sep. 22, 1999 and U.S. patent application Ser. No. 09/400,955 filed Sep. 22, 1999.

BACKGROUND OF THE INVENTION

The present invention provides devices and methods for the endoluminal placement of prostheses, particularly within the vascular system for the treatment of cardiovascular disease, such as vascular stenoses, dissections and other tissue separation conditions, aneurysms, and the like. The apparatus and methods, however, are also useful for placement in other body lumens, such as the ureter, urethra, biliary tract, gastrointestinal tract and the like, for the treatment of other conditions which may benefit from the introduction of a reinforcing or protective structure within the body lumen. The prostheses will be placed endoluminally. As used herein, "endoluminally" will mean placement by percutaneous or cutdown procedures, wherein the prosthesis is transluminally advanced through the body lumen from a remote location to a target site in the lumen. In vascular procedures, the prostheses will typically be introduced "endovascularly" using a catheter over a guidewire under fluoroscopic guidance. The catheters and guidewires may be introduced through conventional access sites to the vascular system, such as through the femoral artery, or brachial and subclavian arteries, for access to the target site.

An endoluminal prosthesis typically comprises at least one radially expansible, usually cylindrical, body segment. By "radially expansible," it is meant that the body segment can be converted from a small diameter configuration (used for endoluminal placement) to a radially expanded, usually cylindrical, configuration which is achieved when the prosthesis is implanted at the desired target site. The prosthesis may be non-resilient, e.g., malleable, thus requiring the application of an internal force to expand it at the target site. Typically, the expansive force can be provided by a balloon catheter, such as an angioplasty balloon for vascular procedures. Alternatively, the prosthesis can be self-expanding. Such self-expanding structures may be provided by a temperature-sensitive superelastic material, such as Nitinol, which naturally assumes a radially expanded condition once an appropriate temperature has been reached. The appropriate temperature can be, for example, a temperature slightly below normal body temperature; if the appropriate temperature is above normal body temperature, some method of heating the structure must be used. Another type of self-expanding structure uses resilient material, such as a stainless steel or superelastic alloy, and forming the body segment so that it possesses its desired, radially-expanded diameter when it is unconstrained, e.g., released from radially constraining forces of a sheath. To remain anchored in the body lumen, the prosthesis will remain partially constrained by the lumen. The self-expanding prosthesis can be delivered in its radially constrained configuration, e.g. by placing the prosthesis within a delivery sheath or tube and retracting the sheath at the target site. Such general aspects of construction and delivery modalities are well-known in the art.

The dimensions of a typical endoluminal prosthesis will depend on its intended use. Typically, the prosthesis will have a length in the range from 0.5 cm to 10 cm, usually being from about 0.8 cm to 5 cm, for vascular applications. The small (radially collapsed) diameter of cylindrical prostheses will usually be in the range from about 1 mm to 10 mm, more usually being in the range from 1.5 mm to 6 mm for vascular applications. The expanded diameter will usually be in the range from about 2 mm to 50 mm, preferably being in the range from about 25 mm to 45 mm for aortic applications.

One type of endoluminal prosthesis includes both a stent component and a graft component. These endoluminal prostheses are often called stent grafts. A stent graft is typically introduced using a catheter with both the stent and graft in contracted, reduced-diameter states. Once at the target site, the stent and graft are expanded. After expansion, the catheter is withdrawn from the vessel leaving the stent graft at the target site. Grafts may be made of, for example, PTFE, ePTFE or Dacron® polyester.

Grafts are used within the body for various reasons, such as to repair damaged or diseased portions of blood vessels such as may be caused by injury, disease, or an aneurysm. It has been found effective to introduce pores into the walls of the graft to provide ingrowth of tissue onto the walls of the graft. With larger diameter grafts, woven graft material is often used. In small and large diameter vessels, porous fluoropolymers, such as ePTFE, have been found useful.

Coil-type stents can be wound about the catheter shaft in torqued compression for deployment. The coil-type stent can be maintained in this torqued compression condition by securing the ends of the coil-type stent in position on a catheter shaft. The ends are released by, for example, pulling on wires once at the target site. See, for example, U.S. Pat. Nos. 5,372,600 and 5,476,505. Alternatively, the endoluminal prosthesis can be maintained in its reduced-diameter condition by a sleeve; the sleeve can be selectively retracted to release the prosthesis. A third approach is the most common. A balloon is used to expand the prosthesis at the target site. The stent is typically extended past its elastic limit so that it remains in its expanded state after the balloon is deflated and removed. One balloon expandable stent is the Palmaz-Schatz stent available from the Cordis Division of Johnson & Johnson. Stents are also available from Medtronic AVE of Santa Rosa, Calif. and Guidant Corporation of Indianapolis, Indiana.

SUMMARY OF THE INVENTION

The present invention is directed to an endoluminal prosthesis and a method for treating a dissection, as well as other tissue separation conditions, within blood vessels and other tubular body structures, using an endoluminal prosthesis.

A first aspect of the invention is directed to an endoluminal prosthesis which includes a coiled body and a graft material covering at least part of the coiled body to create a coiled stent graft. The average stent graft diameter to turns-width ratio may be about 0.8 to 1 to about 2.4 to 1 when expanded. The average turns-width to stent graft length ratio, when expanded, may be about 1 to 1 to about 1 to 4. Adjacent turns of the stent graft may lie adjacent to, or may be spaced apart from, one another when in the radially expanded condition.

Another aspect of the invention is directed to a method for treating a tissue separation, such as a vascular dissection, within a tubular body structure. The tissue separation condition comprises separated tissue defining a gap between the separated tissue and the remainder of the tubular body structure. The method includes placing an endoluminal prosthesis in a radially contracted condition at a target site, the endoluminal prosthesis comprising a coiled body with a graft material covering at least part of the coiled body to create a coiled stent graft. The stent graft is expanded to a radially expanded condition thereby pressing the separated tissue against the remainder of the tubular body structure.

Other features and advantages of the invention will appear from the following description in which the preferred embodiments have been set forth in detail in conjunction with the accompanying drawings.

BRIEF DESCRIPTION OF THE DRAWINGS

FIGS. 1–1D illustrate four additional designs of stent blanks;

FIG. 7B illustrates the release of the proximal half of the stent graft;

FIG. 7C illustrates the release of the distal half of the stent graft prior to the removal of the catheter shafts;

DESCRIPTION OF THE SPECIFIC EMBODIMENTS

Figure 1:
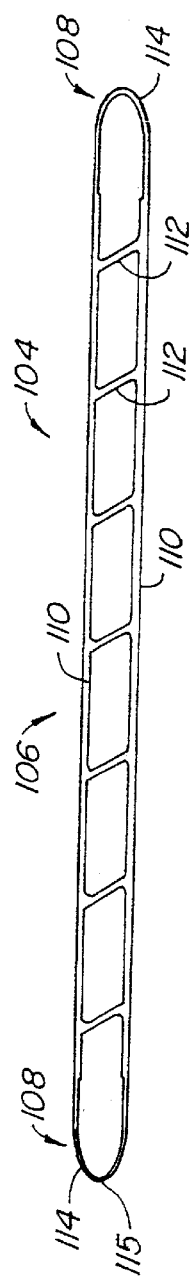
FIG. 1 illustrates a stent blank used to create a coiled stent such as those shown in FIGS. 3, 4 and 5A.
Figure 5A:
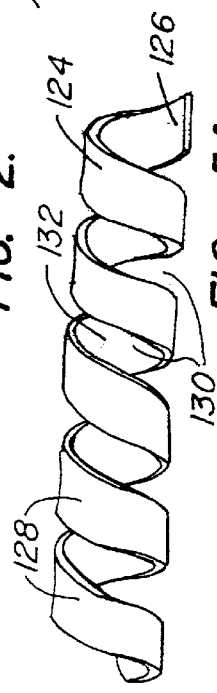
FIG. 5A shows a stent graft similar to that of FIG. 3 but with generally evenly-spaced turns.
Figure 4:
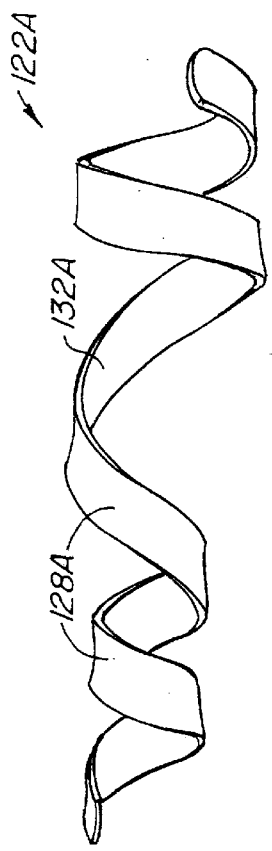
FIG. 4 illustrates a stent graft similar to that of FIG. 3 but in which one end of the stent graft has much greater radially expanded diameter than the other portion to accommodate a vessel having different internal diameters.
Figure 3:
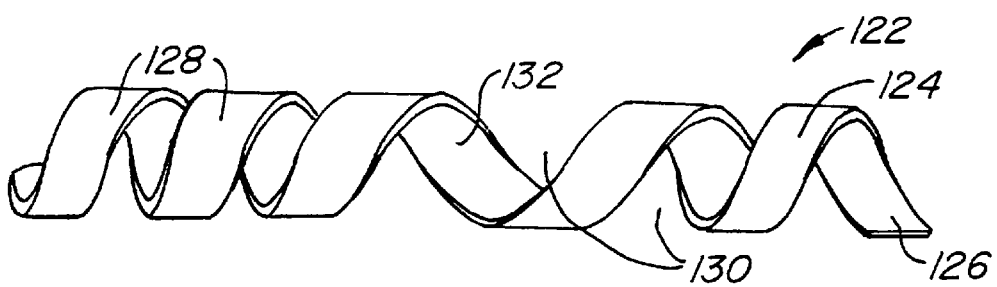
FIG. 3 illustrates a stent graft in a radially expanded condition, the stent graft including a stent similar to that shown in FIG. 1 covered with a sleeve of porous graft material, the stent graft having a central turn with a greatly increased pitch for placement at a branching intersection.

FIG. 1 illustrates a stent blank 104 used to create a coiled stent similar to that shown in FIGS. 3, 4 and 5A. Stent blank 104 includes a main body portion 106 and first and second end portions 108. Main body portion 106 includes side edge or rail elements 110 connected by connector or rung elements 112. Rung elements 112 are, as shown in FIG. 1, at an angle to rail elements 110 so that when stent blank 104 is formed into a coiled stent and tightly wrapped about an introducer catheter, such as in FIG. 17A, rung elements 112 are axially-extending so that they lie flat for a tighter wrap.

End portions 108 are thinner and thus more flexible than main body portion 106. In addition, end portions 108 have an inwardly tapering portion 114 terminating at a blunt tip 115. The shape of end portions 108 and the lessened stiffness of the end portions, compared to body portion 106, help to prevent tissue trauma during use. This type of coiled stent in which the end portions 108 are less stiff than the main body portion 106 can find particular utility in stabilizing a traumatic injury site within a patient, more stiff than main body portion; this embodiment may be useful, for example, when treating occlusive disease on either side of a branch vessel.

Figure 2:
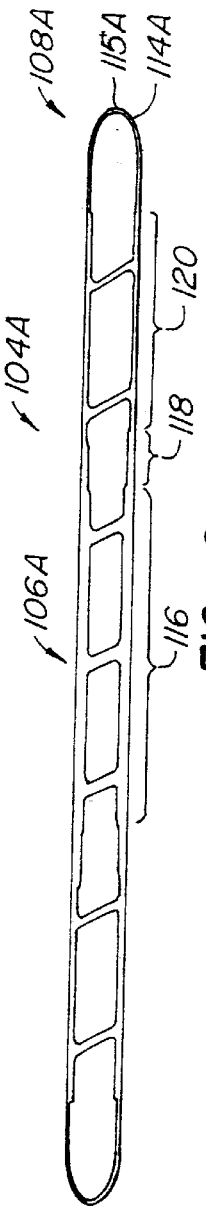
FIG. 2 illustrates a stent blank similar to that of FIG. 1 but having different thickness along its length.

FIG. 2 illustrates a stent blank 104A similar to stent blank 104 of FIG. 1 but in which main body portion 106A has three different radial stiffnesses. That is, main body portion 106A has a first, central longitudinal section 116 of a first, greater stiffness, and second and third longitudinal sections 118, 120 on either side of first section 116. Sections 118, 120 are successively thinner and thus have successively lower radial stiffnesses when stent blank 104A is formed into a coiled stent. End portion 108A acts as the fourth longitudinal section with the least radial stiffness of any of the sections in this embodiment. Instead of a set of generally discrete radial stiffnesses, the radial stiffness could vary continuously along at least part of the length of stent blank 104A, and then along the resulting stent body.

In addition to providing less traumatic end portions 108, 108A, a coiled prosthesis formed from either of stent blanks 104, 104A, when uncoiling, will have a tendency to open up first in the center, because of the greater stiffness at the center, followed by the ends. This helps to reduce the degree to which the end portions 108, 108A are dragged along the surface of the vessel or other hollow body structure as the prosthesis is released.

Figure 1A:
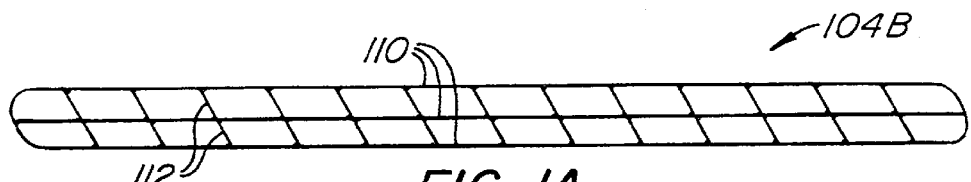
Figure 1B:
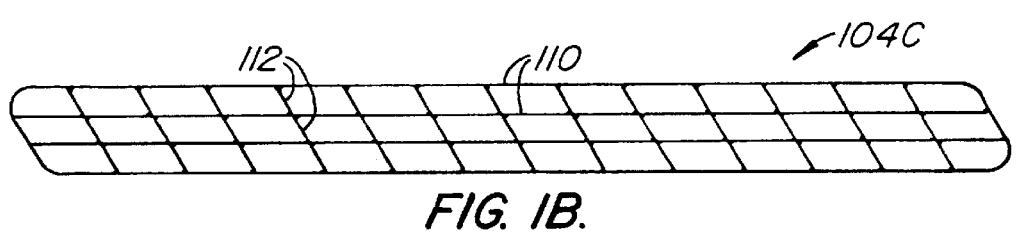
Figure 1C:
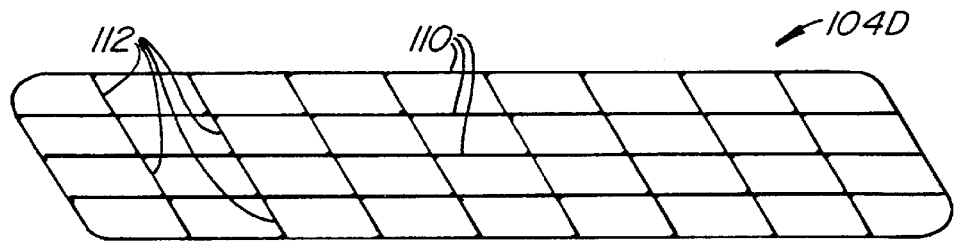
Figure 1D:
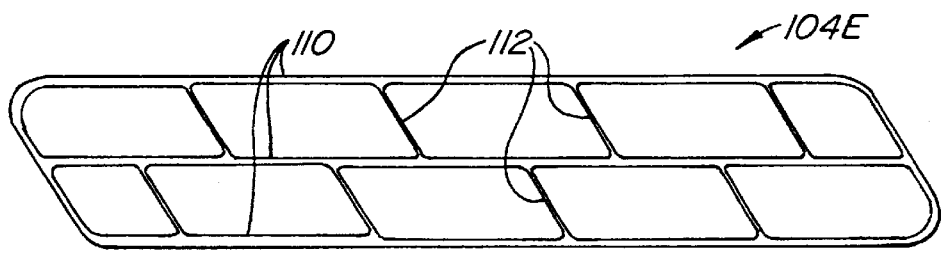
Figure 1E:
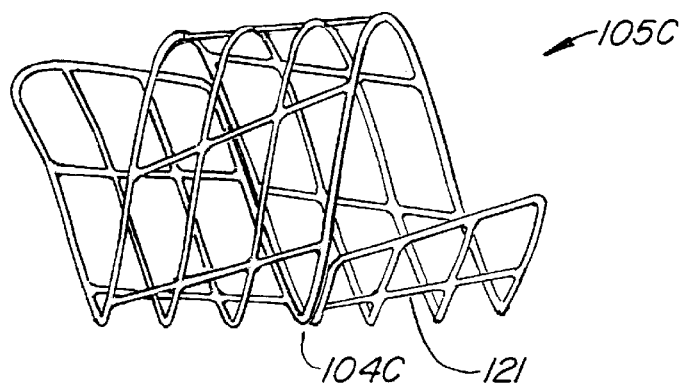
FIG. 1E shows a coiled stent made from the stent blank of FIG. 1B.

FIGS. 1–1D illustrate four different designs of stent blanks 104B–104E. Each of these different stent blanks has at least three rail elements 110 with connector or rung elements 112 extending between the rail elements. In the FIGS. 1–1C embodiments connector elements 112 are aligned while in the 1D embodiment they are offset. The angles of connector elements 112 are such that when the stent blanks are formed into a tight coil during introduction, connector elements 112 are generally axially extending so they lie flat for a tighter wrap. FIG. 1E illustrates a coiled stent 105C made from stent blank 104C with one or more radiopaque markers 121 used to facilitate deployment. Stent blanks 104B–104E are relatively wide so to increase the radial force the coiled stents can apply to the walls of the hollow body organ within which they are to be placed. It has been found that reducing the number of turns for a stent graft having the same axial length helps to increase the user's control of the stent graft during placement. This is important in certain situations, such as when treating a dissection, in particular a vascular dissection such as the aortic dissection shown in FIG. 11 and discussed below. Also, as discussed above, the ends of stent blanks 104B–104E may be rounded or thinned in shape to cause a reduction in the radial force applied at the ends of the stent to help prevent vessel deformation at the ends of the stent.

FIGS. 3, 4, 5 and 5A illustrate four stent graft embodiments 122, 122A, 122B, 122C. Stent graft 122 includes a ladder-type coiled stent formed from stent blank 104 and covered with tubular graft material 124. Graft material 124 is preferably porous PTFE or ePTFE or Dacron® polyester. The ends 126 of graft material 124 are sealed, or for example, by using an adhesive or by placing a suitable heat seal material, such as FEP (fluorinated ethylene propylene) or other thermoplastic materials, between the layers of the graft material 124 and applying heat and pressure. The porous nature of the graft material permits sealing in this manner in spite of the inert nature of PTFE. In addition, a direct bond of the PTFE to itself, via a process known as sintering, may be employed. Other methods for sealing ends 126 could also be used. Coiled stent graft 122 includes a number of spaced apart turns 128 defining a generally helical gap 130 therebetween.

The average width of helical gap 130 is equal to about 0% to 1200% of the average width of turns 128. For some applications the average width of gap of 130 is about 50% to 800% of the average width of turns 128 when stent graft 122 is deployed. For other applications, such as placement at dissections discussed below, gap 130 is closed, that is about 0%.

Stent graft 122 has a generally constant pitch except at its central region. The pitch of a central turn 132 of stent graft 122 is substantially greater than the pitch of its adjacent turns 128 to accommodate placement of stent graft 122 at the intersection of a main or first vessel and a branching vessel as will be discussed in more detail with reference to FIGS. 7–7C.

FIG. 4 illustrates a stent graft 122A in which a central turn 132A also has an increased pitch as opposed to adjacent turns 128A. However, the turns on one side of central turn 132A have a larger fully-expanded diameter than turns on the other side to accommodate transition between smaller and larger diameter vessels.

Figure 5:
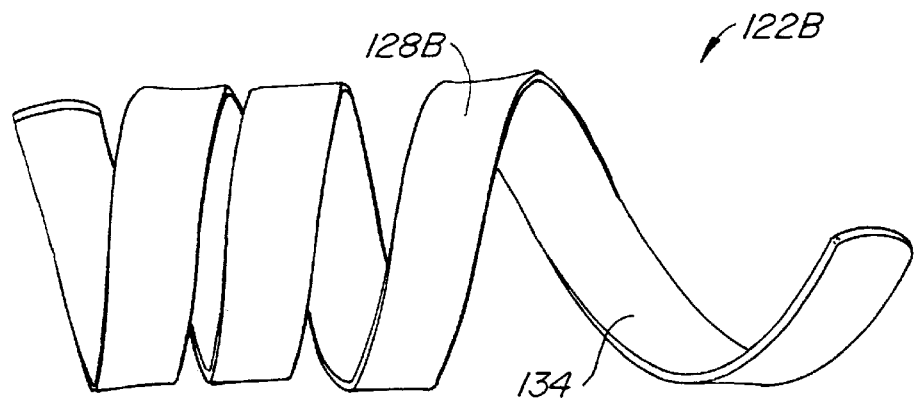
FIG. 5 illustrates an alternative embodiment to the stent graft of FIG. 3 in which the stent graft has a large expanded diameter and also has the one turn with the greater pitch at one end of the stent graft.

FIG. 5 illustrates a stent graft 122B designed for placement with the end turn 134 having a substantially greater pitch than its adjacent turn 128B. Stent graft 122B is used when one end of the stent graft is to be positioned at the intersection and main and branching vessels so that the stent graft extends to one side of the intersection as opposed to both sides as in the embodiments of FIGS. 3 and 4. FIG. 5A illustrates stent graft 122C, which may be used at locations other than bifurcations, having generally uniformly spaced turns 128C.

Figure 5B:
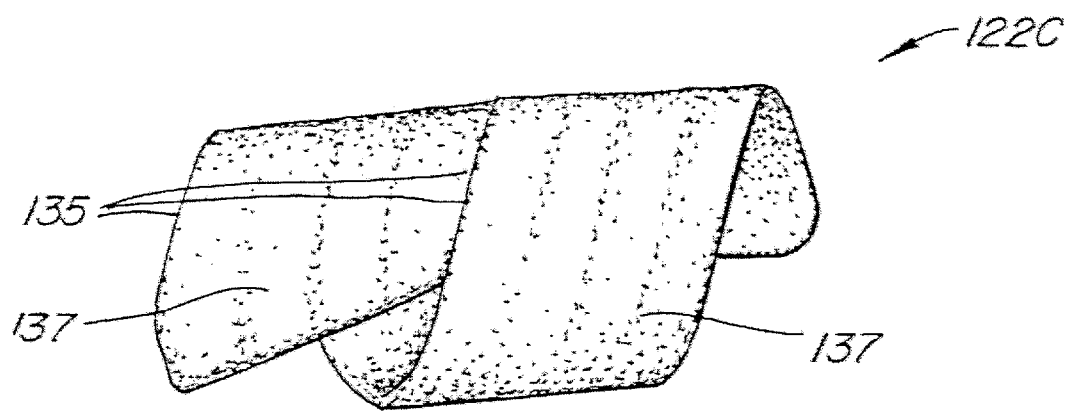
FIGS. 5B and 5C illustrate stent grafts made from the stent blank of FIG. 1C.
Figure 5C:
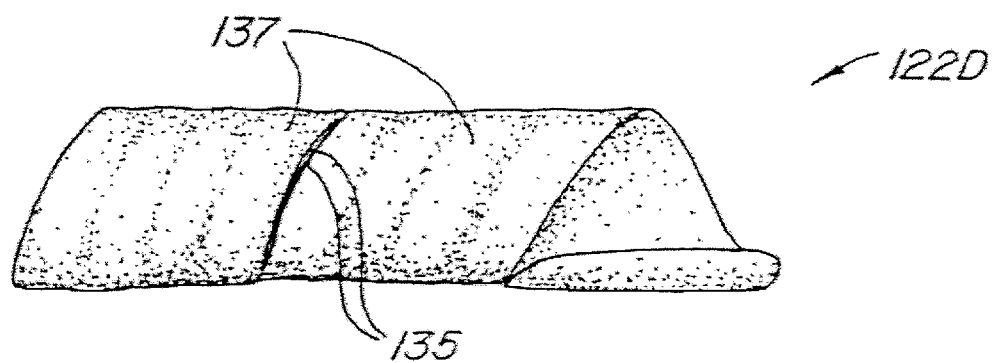

FIGS. 5B and 5C illustrate stent grafts 122C, 112D each made from stent blank 104D of FIG. 1C. Stent grafts 122C, 122D are designed and intended to have the edges 135 of adjacent turns 137 adjacent to one another. Such stent grafts as FIGS. 5B and 5C are intended for use in treating aortic dissections. The combination of having the width of each turn being relatively wide compared to the diameter when in the radial expanded condition, plus the use of abutting or overlapping adjacent edges, combine to make such a stent graft useful when full surface coverage and reasonably higher outward radial force are desired. The width of turns 137 is measured perpendicular to edges 135. Also, fewer turns can make the stent graft easier to control and require fewer rotations of shafts 138, 142 prior to release from catheter 136. Stent grafts 122C, 122D may be characterized by having an average diameter to turns-width ratio, when in their radially expanded conditions, from about 0.1 to 1 to about 2.4 to 1. Stent grafts 122C, 122D may also be characterized by having an average turns-width to stent graft length ratio, when in their radially expanded conditions, from about 1 to 1 to about 1 to 4. In some situations it may not be necessary or desired to have connectors 112 be axially extending when in the tightly wound, radially contracted condition. In some cases connectors 112 could be replaced by other shapes of connectors, such as wave- or undulating-shaped connectors, v-shaped connectors, x-shaped connectors, etc.

Figure 6A:
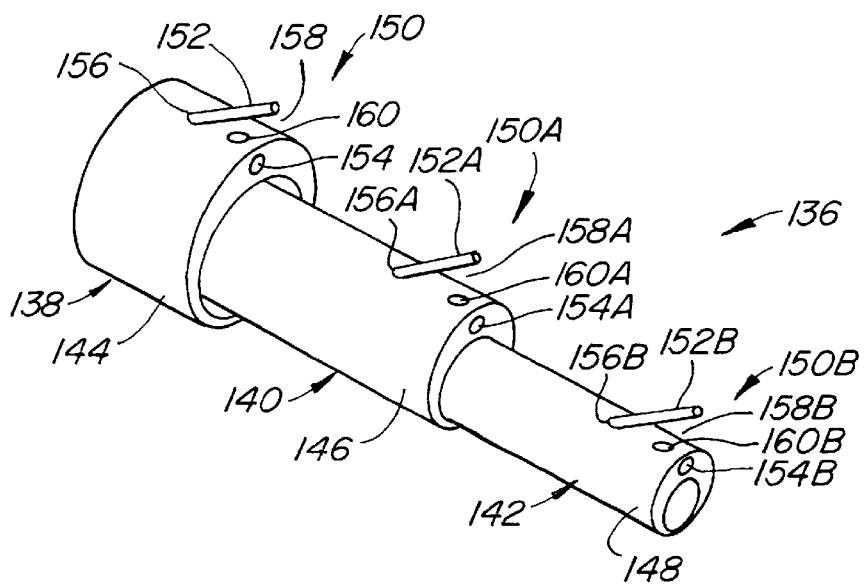
FIG. 6A is an overall view of the distal end of a three-shaft deployment catheter used to deploy the stent grafts of FIGS. 3–5.
Figure 6B:
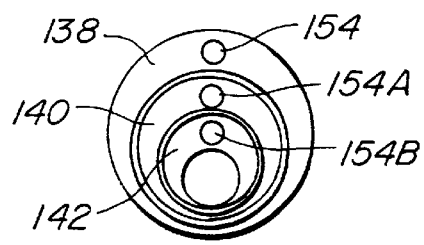
FIG. 6B is an end view of the shafts of 6A.

FIGS. 6–6B illustrate a catheter 136 used for deploying the stent grafts of FIGS. 3 and 4. Catheter 136 includes outer, intermediate and inner rotating, telescoping shafts 138, 140, 142 each having a distal end 144, 146, 148. Each of the shafts has a prosthesis portion holder 150, 150A, 150B at its distal end 144, 146, 148. Prosthesis portion holders 150, 150A, 150B include pull wires 152, 152A, 152B which pass along axially-extending lumens 154, 154A, 154B formed in the body of shafts 138, 140, 142, out of exit holes 156, 156A, 156B, across gaps 158, 158A, 158B and back into reinsertion openings 160, 160A, 160B. Pull wires 152, 152A, 152B pass through and engage different portions of, for example, stent graft 122 and secure those portions of the stent graft to shafts 138, 140, 142. As shown in FIG. 7A, prosthesis portion holder 150B at distal end 148 of inner shaft 142 engages the distal end 166 of stent graft 122. Holders 150, 150A at distal ends 144, 144A of outer and intermediate shafts 138, 140 engage proximal end 168 and central turn 132 of stent graft 122, respectively. One or more of shafts 138, 140, 142 may be braided to enhance torquing stiffness to aid rotation.

Figure 6C:
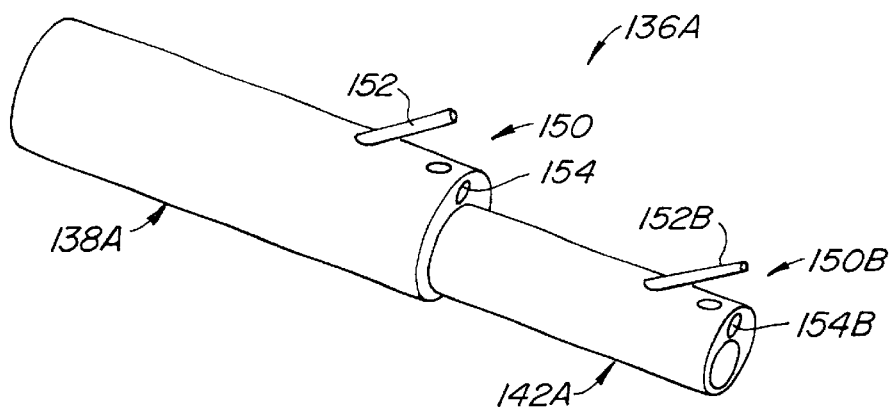
FIG. 6C is an embodiment similar to the catheter of FIG. 6A but including only inner and outer shafts.
Figure 7A:
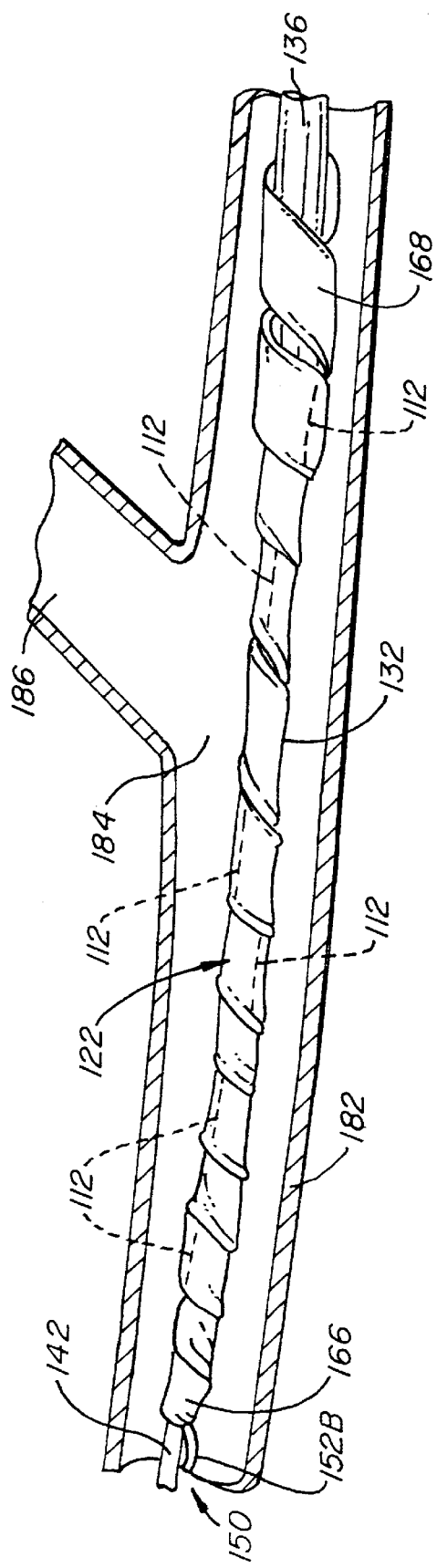
FIG. 7A illustrates the stent graft of FIG. 3 tightly wrapped about the distal end of the catheter of FIGS. 6A and 6B and placed within a vessel with the intermediate portion of the stent graft at the intersection of the main and branching vessels.

FIG. 6C illustrates the distal end of a catheter 136A including only two shafts, outer shaft 138A and inner shaft 142A. Catheter 136A is typically used when placing an endoluminal prosthesis of the type which does not have a central turn with an increased pitch, such as those of FIGS. 5, 5A, 5B and 5C, and thus does not need a catheter with an intermediate shaft.

Figure 6D:
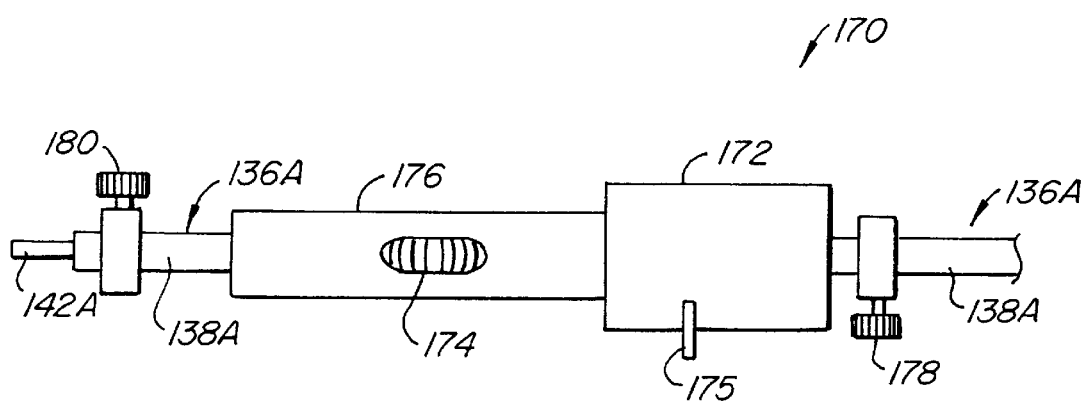
FIG. 6D illustrates a proximal end adapter mounted to the proximal end of the catheter of FIG. 6C.
Figure 6E:
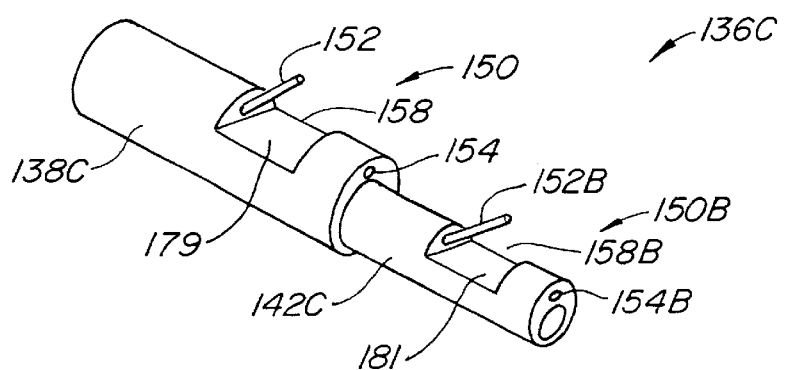
FIG. 6E illustrates an alternative embodiment of the catheter of FIG. 6C.

FIG. 6D illustrates, in a simplified form, a proximal end adapter 170 mounted to the proximal end of catheter 136A of FIG. 6C. Proximal end adapter 170 includes distal and proximal portions 172, 176 through which catheter 136A passes. Proximal end adapter 170 provides for the rotation of either or both shafts 138A, 142A through the manipulation of thumb wheel 174 mounted to portion 176. A flip lever 175 extends from distal portion 172 and is movable between secured and released positions to either secure shafts 138A, 142A to one another or to permit shafts 138A, 142A to move axially relative to one another. Pull wires 152, 152B are normally secured to their respective shafts 138A, 142A by deployment knobs 178, 180; pulling on deployment knobs 178, 180 releases pull wires 152, 152B, respectively to permit the pull wires to be pulled to release the endoluminal prosthesis from the appropriate holder 150, 150B.

Figure 6F:
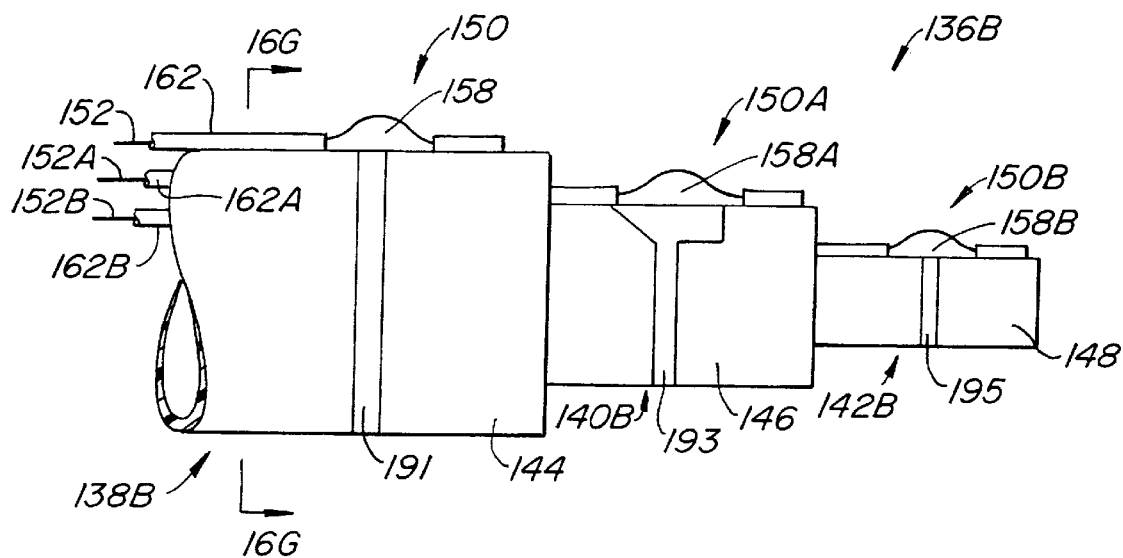
FIGS. 6F and 6G are simplified side and cross-sectional views of a further alternative embodiment of the catheter of FIGS. 6A and 6B.
Figure 6G:
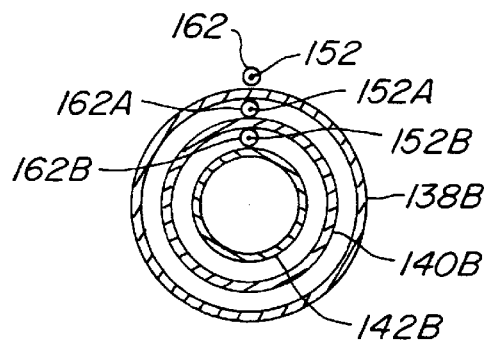

FIGS. 6F and 6G illustrate a further three-shaft embodiment of the invention similar to the three-shaft embodiment of FIGS. 6A and 6B. Instead of using lumens 154 to house pull wires 152, tubular members 162, 162A, 162B, typically hypotubes, could be secured to the outside of the shafts 138B, 140B, 142B. Gaps or breaks are provided at the distal ends of hypotubes 162, 162A, 162B to define the gaps 158, 158A, 158B.

Figure 8:
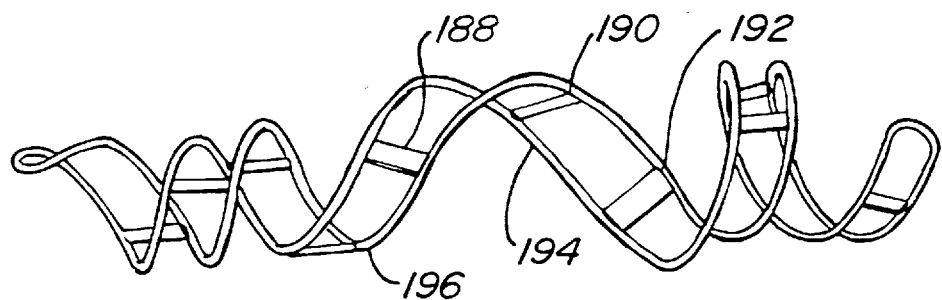
FIGS. 8 and 9 illustrate the placement of radiopaque marks at different positions along a coiled ladder-type stent having a central turn with a greatly increased pitch.
Figure 9:
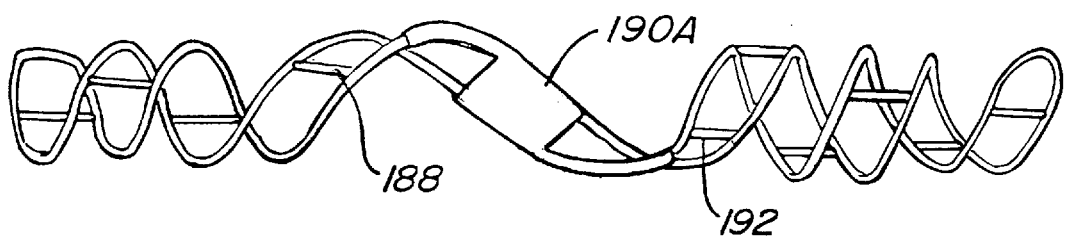

FIG. 7A shows stent graft 122 of FIG. 3 tightly wrapped about catheter 136. Distal end 166, proximal end 168 and central turn 132 of stent graft 122 are secured to distal ends 148, 144 and 146 of inner, outer and intermediate shafts 142, 138 140 by prosthesis portions holders 150. Stent graft 122 is housed within a main vessel 182 with central turn 132 aligned with the intersection 184 of main vessel 182 and branching vessel 186. To help ensure proper placement of central turn 132 at intersection 184, stent graft 122 has one or more remote visualization markers at or adjacent to turn 132. Radiopaque markers 188, 190 192 are shown in FIG. 8 at distal, intermediate and proximal portions of the central turn 194 of stent 196. Radiopaque markers may be shaped to provide, information as to both location and orientation of stent 196 on the catheter. For example, radiopaque marker 190A of FIG. 9 has a broad central portion 190B extending between rail elements 110 and arm portions 190C extending along rail elements 110; this permits marker 190A to provide both location and orientation information about stent 196A. Orientation marker 190A is configured so that the viewer can determine whether the turn is facing the viewer or is away from the viewer based upon the marker's orientation. Various other marker shapes to provide both location and orientation can also be used.

Figure 10:
FIG. 10 illustrates one example of a radiopaque marker shaped to permit the determination of the orientation of the prosthesis as well as its location.

Radiopaque markers may also be used on the placement catheter itself. For example, radiopaque markers 191, 193, 195 are used on shafts 138B, 140B, 142B aligned with their respective holders 150, 150A, 150B, as shown in FIG. 6F, to indicate the location of the holders. Radiopaque marker 193 is shown to be configured as an orientation specific marker to help in the proper placement of the prosthesis. FIG. 10 illustrates the shape of an orientation-specific radiopaque marker 197 which could be placed, for example, on shafts 138, 140, 142 at one or more of the holders 150 of the embodiments of FIGS. 6A, 6C and 6E. Radiopaque or other remote visualization markers may also be used at other positions along the endoluminal prosthesis, such as at each end, or along the placement catheter.

FIG. 7B illustrates the release of proximal end 168 of stent graft 122 while FIG. 7C illustrates the subsequent release of distal end 166 of stent graft 122. It should be noted that central turn 132 remains secured to intermediate shaft 140 while the distal and proximal ends 166, 168 of stent graft 122 are released to ensure that the open region of central turn 122 remains facing intersection 184 to help ensure substantially unrestricted fluid flow between main vessel 182 and branching vessel 186. It should also be noted that prior to releasing the stent graft, the number of turns can be increased or decreased by the relative rotation of shafts 138, 140 and 142. Also, the length of stent graft 122 can be changed by the relative axial sliding motion among outer, intermediate and inner shafts 138, 140, 142. For example, instead of simply releasing proximal end 168 of stent graft 122 to the position shown in FIG. 7B, it may be desired to rotate outer shaft relative to intermediate shaft 140, keeping intermediate and inner shafts 140, 142 stationary so to unwind the proximal half of the stent graft to ensure that the stent graft is properly positioned prior to releasing the stent graft. Similarly, both outer shaft and inner shafts can be rotated while maintaining intermediate shaft stationary to create the expanded diameter condition of FIG. 7 prior to releasing any portion of the stent graft. In this way the physician can ensure that stent graft 122 is properly positioned, especially with respect to central turn 132. If necessary or desired, intermediate shaft 140 could be, for example, rotated relative to outer and inner shafts 138, 142 to help properly position or reposition central turn 132.

FIG. 7A also shows how by properly selecting the angle of connector elements 112 relative to side elements 110 for a placement catheter of a particular outside diameter, connector elements 112, indicated by dashed lines in FIG. 7A, will lie generally parallel to the axis of stent graft 122. This permits connector element 112 to lie closer to catheter 136, to provide a much smoother wrap when in its contracted, reduced-diameter state, than would result if connector elements were not generally parallel to the axis in such a state. This axial orientation can be contrasted with the off-axis orientation of connectors 112 when in the expanded diameter state of FIG. 7C. The smoother outer surface of stent graft 122 enhances the ease of insertion of the stent graft within a hollow body organ, such as blood vessel 182.

Figure 7E:
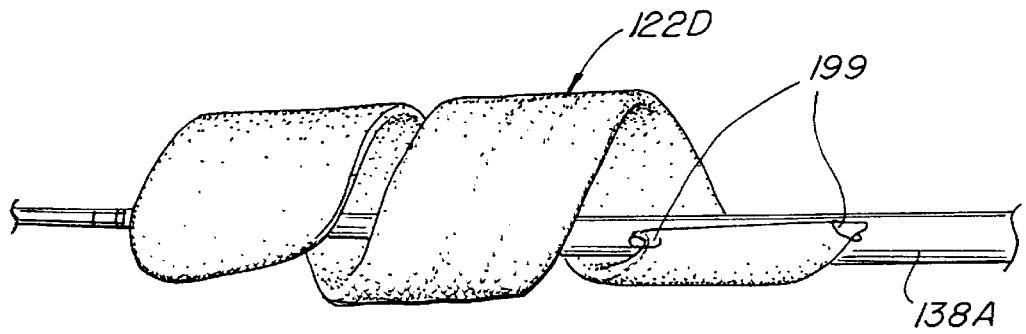
FIG. 7E illustrates the stent graft of FIG. 7D with the distal end of the stent graft released from the catheter and the proximal end of the stent graft releasably secured to the catheter at two positions.
Figure 7D:
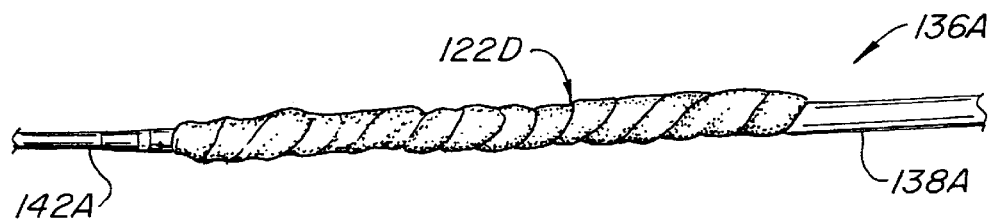
FIG. 7D illustrates the stent graft of FIG. 5C tightly wrapped about a placement catheter.

FIG. 7D illustrates stent graft 122D of FIG. 5C tightly wrapped about placement catheter, 136A of FIG. 6C with the proximal end of stent graft 122D secured to outer catheter shaft 138A and the distal end of stent graft 122D secured to inner catheter shaft 142A. FIG. 7E illustrates the structure of FIG. 7D after pull wire 152B has been pulled to release the distal end of stent graft 122D. Soon thereafter pull wire 152 will be pulled to release the proximal end of stent graft 122D from outer catheter shaft 138A. Because of the width of each turn of stent graft 122D, each pull wire 152, 152B passes through two positions 199 along an end of stent graft 122D to ensure that the stent graft lies tightly against catheter 136A during delivery.

As discussed above, stent graft 122D is placed in a radially contracted condition by rotating inner and outer catheter shafts 138A, 142A relative to one another. Once in position for deployment, catheter shafts 138A, 142A are rotated relative to each other to open stent graft 122D. Shafts 138A, 142A can also be moved longitudinally (axially) relative to one another to allow one to change the pitch and ensure that edges 135 of turns 137 of stent graft 122 will be adjacent to one another when fully deployed, as is often desired. At any point the operator can decide to retighten stent graft 122D, placing it in a radially contracted condition, to reposition the stent graft or change the pitch so long as pull wires 152, 152B have not been removed from the ends of the stent graft. Proper placement of the graft 122D, including ensuring that the edges lie adjacent to one another, can be aided by the used of radiopaque markers 121. See FIG. 1E.

Figure 11:
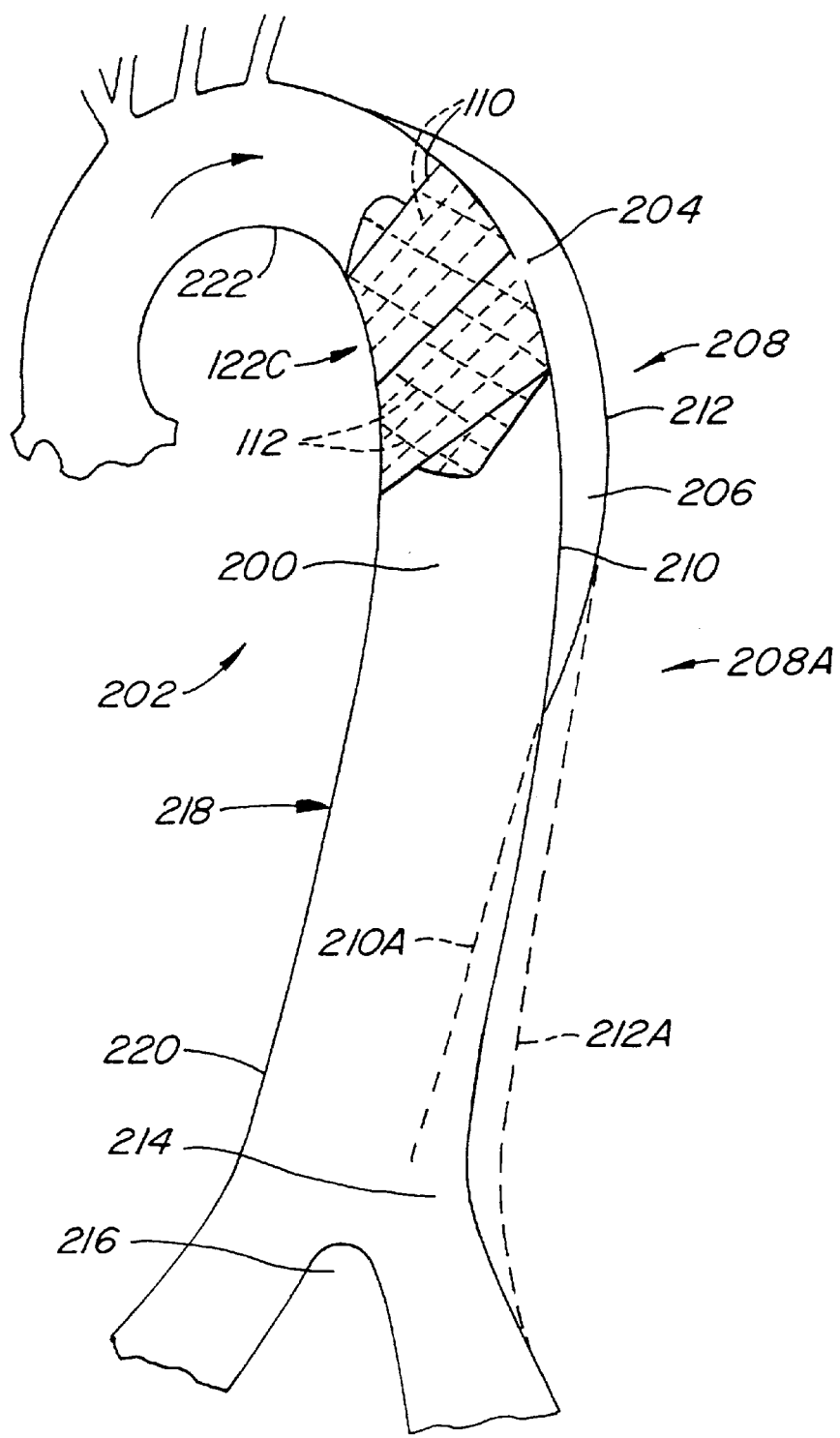
FIG. 11 illustrates of the stent graft of FIG. 5B within the true lumen of the aortic arch at the entry of an aortic dissection, an alternative aortic dissection being shown in dashed lines.

FIG. 11 illustrates the placement of stent graft 122C within the true lumen 200 of an aortic arch 202 so to cover the entry 204 into a false lumen 206 created by an aortic dissection 208. Aortic dissections are of various type but all include a false lumen caused by separation of the lining, such as intimal lining 210, from the remainder of the wall, such as wall 212 of the hollow body structure, together with an entry formed through the separated lining into the false lumen. Aortic dissections, as well as other dissections, may be of the type with a single entry 204 or may include, for example, an entry and an exit. An alternative dissection 208A is suggested by the dashed lines in FIG. 11 indicating an extension of aortic dissection 208 from the solid line portion down to an exit 214 adjacent bifurcation 216. While it may be possible to close both entry 204 and exit 214 using one or more stent grafts, it may not be necessary or desirable. Also, it may not be necessary to cover either the entrance and/or any exit to a false lumen with the stent graft to effectively treat the dissection. Stent graft 122C also has dashed lines indicating the locations of rail elements 110 and connector elements 112 of the stent.

Figure 12:
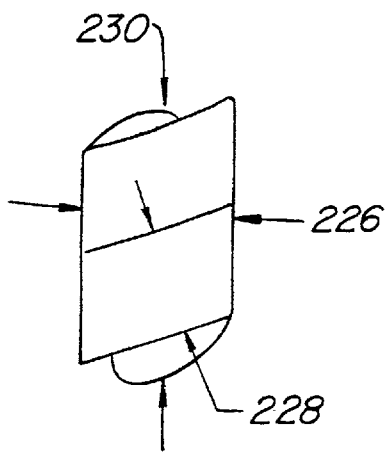
FIG. 12 illustrates various dimensions for the stent graft of FIG. 11.

Stent graft 122c may have at most two full turns when in the radially-expanded condition. The average ratio of stent graft diameter 226, see FIG. 12, to turns-width 228 may be about 0.8 to 1 to about 2.4 to 1 when expanded. The average ratio of turns-width 228 to stent graft length 230, when expanded, may be about 1 to 1 to about 1 to 4.

Stent graft 122C is used with a thoracic level aortic dissection. Stent grafts may be used with dissections at other levels along aorta 218, such as at the abdominal level 220 or along the arch 222. When a stent graft is used at arch 222, or at other hollow body regions with one or more branches, stent grafts having one or more enlarged gaps, see FIGS. 3, 4 and 7C, may be used to help prevent obstruction of the branching vessel.

Stent grafts, such as those of FIGS. 5B and 5C, may be used to help repair various dissections other than aortic dissections. In particular, such stent grafts may be used for other types of vascular dissections and dissections in other hollow body organs within which dissections may be found. The dissections may be created as a result of non-penetrating trauma or invasive trauma as well as biological reasons, such as disease, stress, congenital disorders, etc.

Modification and variation can be made to the above described invention without departing from the subject of the invention as defined in the following claims. For example, connectors 112 could be oriented perpendicular to rail elements 110, graft material 124 could be placed upon only a portion of the underlying stent or on only one side of the underlying stent. Placement catheter 136 could include fewer or additional telescoping rotatable shafts. The telescoping shafts may not need to be coaxial shafts slidable within or over one another; the telescoping shafts could be, for example, solid and/or tubular elongate members positioned side-by-side. Holders 150 could be constructed differently; for example, if the sequence of releasing the prosthesis is known it may be possible to use a single pull wire instead of three separate pull wires.

Any and all patents, applications, and printed publications referred to above are incorporated by reference.

What is claimed is:

1. A method for treating a tissue separation condition within a tubular body structure, the tissue separation condition comprising separated tissue defining a gap between the separated tissue and the remainder of the tubular body structure, comprising;

placing an endoluminal prosthesis in a radially contracted condition at a tissue separation condition target site, the target site being an entry opening into a false lumen defined between the separated tissue of a dissection and the remainder of the tubular body structure, the endoluminal prosthesis comprising:
a coiled body;
a graft material covering at least a part of the coiled body to create a coiled stent graft movable between radially expanded and radially contracted conditions, said coiled stent graft comprising turns, said turns having edges and a width measured perpendicular to said edges, said stent comprising turns, said turns having edges and a width measured perpendicular to said edges, said stent graft placeable in the radially contracted condition for placement and in the radially expanded condition for use; and
said stent graft having in an average turns-width to stent graft length ratio from about 1 to 1 to about 1 to 4 when in the radially expanded condition; and
expanding the stent graft towards the radially expanded condition thereby pressing against the separated tissue to help press the separated tissue against the remainder of the tubular body structure.

2. A method according to claim 1 wherein the placing step is carried out using an endoluminal prosthesis constructed so that when in the radially expanded condition, said stent graft has an average stent graft diameter to turns-width ratio from about 0.8 to 1 to about 2.4 to 1.

3. A method according to claim 1 wherein the placing step is carried out using an endoluminal prosthesis constructed so that adjacent turns of the coiled stent graft lie adjacent to one another when in the radially expanded condition.

4. A method according to claim 1 wherein the placing step takes place within a vascular structure.

5. A method according to claim 1 wherein the placing step is carried out using a coiled stent graft having a gap between adjacent turns thereof.

6. A method for treating a tissue separation condition within a tubular body structure, the tissue separation condition comprising separated tissue defining a gap between the separated tissue and the remainder of the tubular body structure, comprising:

placing an endoluminal prosthesis within the aortic arch in a radially contracted condition at a tissue separation condition target site, the endoluminal prosthesis comprising:
a coiled body;
a graft material covering at least a part of the coiled body to create a coiled stent graft movable between radially expanded and radially contracted conditions, said coiled stent graft comprising turns, said turns having edges and a width measured perpendicular to said edges, said stent graft placeable in the radially contracted condition for placement and in the radially expanded condition for use; and
said stent graft having in an average turns-width to stent graft length ratio from about 1 to 1 to about 1 to 4 when in the radially expanded condition; and
expanding the stent graft towards the radially expanded condition thereby pressing against the separated tissue to help press the separated tissue against the remainder of the tubular body structure.

7. A method for treating a tissue separation condition within a tubular body structure, the tissue separation condition comprising separated tissue defining a gap between the separated tissue and the remainder of the tubular body structure, comprising:

placing an endoluminal prosthesis in a radially contracted condition at a tissue separation condition target site at a dissection site, comprising an entry into and an exit out of a false lumen defined between the separated tissue and the remainder of the tubular body structure, with the target site being the entry, the endoluminal prosthesis comprising:
a coiled body;
a graft material covering at least a part of the coiled body to create a coiled stent graft movable between radially expanded and radially contracted conditions, said coiled stent graft comprising turns, said turns having edges and a width measured perpendicular to said edges, said stent graft placeable in the radially contracted condition for placement and in the radially expanded condition for use; and said stent graft having in an average turns-width to stent graft length ratio from about 1 to 1 to about 1 to 4 when in the radially expanded condition; and expanding the stent graft towards the radially expanded condition thereby pressing against the separated tissue to help press the separated tissue against the remainder of the tubular body structure.

8. A method for treating a tissue separation condition within a tubular body structure, the tissue separation condition comprising separated tissue defining a gap between the separated tissue and the remainder of the tubular body structure, comprising:

placing an endoluminal prosthesis, comprising a coiled stent graft having a gap between adjacent turns thereof, in a radially contracted condition at a tissue separation condition target site;

positioning the stent graft at a branching vessel target site with said gap generally aligned with a branching vessel, the endoluminal prosthesis comprising:
a coiled body;
a graft material covering at least a part of the coiled body to create a coiled stent graft movable between radially expanded and radially contracted conditions, said coiled stent graft he is comprising turns, said turns having edges and a width measured perpendicular to said edges, said stent graft placeable in the radially contracted condition for placement and in the radially expanded condition for use; and
said stent graft having in an average turns-width to stent graft length ratio from about 1 to 1 to about 1 to 4 when in the radially expanded condition; and
expanding the stent graft towards the radially expanded condition thereby pressing against the separated tissue to help press the separated tissue against the remainder of the tubular body structure.

9. A method for treating a dissection within the aortic arch of a patient comprising:

obtaining an endoluminal prosthesis;
placing the endoluminal prosthesis within an aortic arch in a radially contracted condition at a target site, the target site being an entry opening into a false lumen, the dissection comprising separated tissue defining the false lumen between the separated tissue and the remainder of the aortic arch, the endoluminal prosthesis comprising:
a coiled body; and
a graft material covering at least a part of the coiled body to create a coiled stent graft movable between radially expanded and radially contracted conditions, adjacent turns of the coiled stent graft lying adjacent to one another when in the radially expanded condition, said turns having edges and a width measured perpendicular to said edges, said stent graft placeable in the radially contracted condition for placement and in the radially expanded condition for use; and
the obtaining step being carried out so that when in the radially expanded condition, said stent graft has an average turns-width to stent graft length ratio from about 1 to 1 to about 1 to 4;
expanding the stent graft towards the radially expanded condition thereby pressing against the separated tissue to help press the separated tissue against the remainder of the tubular body structure.

10. A method according to claim 9 wherein the obtaining step is carried out so that when in the radially expanded condition, said stent graft has an average stent graft diameter to turns width ratio from about 0.8 to 1 to about 2.4 to 1.

11. A method for treating a tissue separation condition within a tubular body structure, the tissue separation condition comprising separated tissue defining a gap between the separated tissue and the remainder of the tubular body structure, comprising:

placing an endoluminal prosthesis in a radially contracted condition at a tissue separation condition target site, the endoluminal prosthesis comprising:
a coiled body;
a graft material covering at least a part of the coiled body to create a coiled stent graft movable between radially expanded and radially contracted conditions, adjacent turns of the coiled stent graft lying spaced apart from one another when in the radially expanded condition to define a gap therebetween, said turns having edges and a width measured perpendicular to said edges, said stent graft placeable in the radially contracted condition for placement and in the radially expanded condition for use; and
said stent graft having an average turns-width to stent graft length ratio from about 1 to 1 to about 1 to 4 when in the radially expanded condition; and
expanding the stent graft towards the radially expanded condition thereby pressing against the separated tissue to help press the separated tissue against the remainder of the tubular body structure.

12. A method according to claim 11 wherein the placing step is carried out using an endoluminal prosthesis constructed so that when in the radially expanded condition, said stent graft has an average stent graft diameter to turns-width ratio from about 0.8 to 1 to about 2.4 to 1.

13. A method according to claim 11 wherein the placing step takes place within a vascular structure.

14. A method according to claim 13 wherein the placing step takes place within the aortic arch.

15. A method according to claim 11 wherein the placing step takes place with the target site being an entry opening into a false lumen defined between the separated tissue of a dissection and the remainder of the tubular body structure.

16. A method according to claim 11 further comprising positioning the stent graft at a branching vessel target site with said gap generally aligned with a branching vessel.

17. A method for treating a dissection within the aortic arch of a patient comprising:

obtaining an endoluminal prosthesis;
placing the endoluminal prosthesis within an aortic arch in a radially contracted condition at a target site, the target site being an entry opening into a false lumen, the dissection comprising separated tissue defining the false lumen between the separated tissue and the remainder of the aortic arch, the endoluminal prosthesis comprising:
a coiled body; and
a graft material covering at least a part of the coiled body to create a coiled stent graft movable between radially expanded and radially contracted conditions, adjacent turns of the coiled stent graft lying spaced apart from one another to define a gap therebetween when in the radially expanded condition, said turns having edges and a width measured perpendicular to said edges, said stent graft placeable in the radially contracted condition for placement and in the radially expanded condition for use; and expanding the stent graft towards the radially expanded condition thereby pressing against the separated tissue to help press the separated tissue against the remainder of the tubular body structure;

the obtaining step being carried out so that when in the radially expanded condition, said stent graft has an average stent graft diameter to turns width ratio from about 0.8 to 1 to about 2.4 to 1 and an average turns-width to stent graft length ratio from about 1 to 1 to about 1 to 4.

* * * * *